(12) United States Patent
Murakami

(10) Patent No.: US 7,808,631 B2
(45) Date of Patent: Oct. 5, 2010

(54) STIRRER AND ANALYZER

(75) Inventor: Miyuki Murakami, Hino (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/199,577

(22) Filed: Aug. 27, 2008

(65) Prior Publication Data

US 2008/0316477 A1 Dec. 25, 2008

Related U.S. Application Data

(63) Continuation of application No. PCT/JP2006/324672, filed on Dec. 11, 2006.

(30) Foreign Application Priority Data

Feb. 28, 2006 (JP) ............................. 2006-053440

(51) Int. Cl.
*G01N 21/01* (2006.01)
*G01N 21/59* (2006.01)
*B01F 11/00* (2006.01)

(52) U.S. Cl. .................... 356/244; 356/246; 422/82.05; 422/68.1; 166/116; 166/108; 166/127

(58) Field of Classification Search ................. 356/244, 356/246, 432–444; 422/63, 64, 67, 68.1, 422/82.05; 366/116, 108, 127
See application file for complete search history.

(56) References Cited

U.S. PATENT DOCUMENTS

| 4,451,433 | A | * | 5/1984 | Yamashita et al. ............. 422/63 |
|---|---|---|---|---|
| 5,151,883 | A | * | 9/1992 | Mitome ........................ 367/138 |
| 5,152,180 | A | * | 10/1992 | Waldhauer, Jr. ............... 73/579 |
| 5,736,100 | A | * | 4/1998 | Miyake et al. ................. 422/64 |
| 6,057,773 | A | * | 5/2000 | Shukla et al. ................. 340/623 |
| 6,737,021 | B2 | * | 5/2004 | Watari et al. .................. 422/63 |
| 6,875,401 | B1 | * | 4/2005 | Suzuki et al. .................. 422/63 |
| 6,912,891 | B2 | * | 7/2005 | Coupland et al. ........... 73/64.53 |
| 7,198,813 | B2 | * | 4/2007 | Wixforth ...................... 427/2.1 |
| 2004/0050836 | A1 | * | 3/2004 | Nesbitt et al. ................ 219/201 |
| 2007/0002678 | A1 | | 1/2007 | Murakami |
| 2008/0074945 | A1 | * | 3/2008 | Murakami et al. ........... 366/110 |
| 2008/0095667 | A1 | * | 4/2008 | Murakami et al. .......... 422/68.1 |

FOREIGN PATENT DOCUMENTS

| JP | 2000-146986 | | 5/2000 |
|---|---|---|---|
| JP | 2000146986 | A * | 5/2000 |
| JP | 3168886 | | 3/2001 |
| JP | 2005-257406 | | 9/2005 |
| WO | WO 01/77691 | A1 | 10/2001 |

OTHER PUBLICATIONS

English-language abstract only of Japanese Patent Application Publication No. 08-146007 dated Jun. 7, 1996.

* cited by examiner

*Primary Examiner*—Sang Nguyen
(74) *Attorney, Agent, or Firm*—Townsend and Townsend and Crew, LLP

(57) ABSTRACT

A stirrer includes a vessel for holding a liquid to be stirred; and a sound wave generator that irradiates the liquid with a sound wave to stir the liquid by the sound wave. The sound wave generator includes a piezoelectric substrate, and a sound generating element provided on the piezoelectric substrate and arranged outside the vessel so as to be adjacent to the liquid across the vessel and the piezoelectric substrate to generate a sound wave for stirring the liquid.

18 Claims, 16 Drawing Sheets

STIRRER AND ANALYZER

CROSS-REFERENCE TO RELATED APPLICATIONS

This application is a continuation of PCT international application Ser. No. PCT/JP2006/324672 filed Dec. 11, 2006 which designates the United States, incorporated herein by reference, and which claims the benefit of priority from Japanese Patent Application Nos. 2006-053440, filed Feb. 28, 2006, the entire contents of which are incorporated herein by reference.

BACKGROUND OF THE INVENTION

1. Field of the Invention

The present invention relates to a stirrer and an analyzer.

2. Description of the Related Art

Conventionally, an analyzer analyzes constituent concentrations and the like in a specimen by stirring a liquid sample containing the specimen and a reagent to cause a reaction thereof and analyzing a reaction mixture. As a stirrer for stirring a liquid sample, one that stirs a liquid sample containing a specimen and a reagent in a noncontact fashion by sound waves in order to avoid so-called carry-over is known (See, for example, Japanese Patent Application Laid-open No. 2005-257406).

SUMMARY OF THE INVENTION

A stirrer according to one aspect of the present invention includes a vessel for holding a liquid to be stirred; and a sound wave generator that irradiates the liquid with a sound wave to stir the liquid by the sound wave. The sound wave generator includes a piezoelectric substrate, and a sound generating element provided on the piezoelectric substrate and arranged outside the vessel so as to be adjacent to the liquid across the vessel and the piezoelectric substrate to generate a sound wave for stirring the liquid.

An analyzer according to another aspect of the present invention is for stirring and reacting different liquids to measure an optical property of a reaction liquid, and thus to analyze the reaction liquid. The analyzer uses the stirrer according to the present invention to optically analyze the reaction liquid containing a specimen and a reagent.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
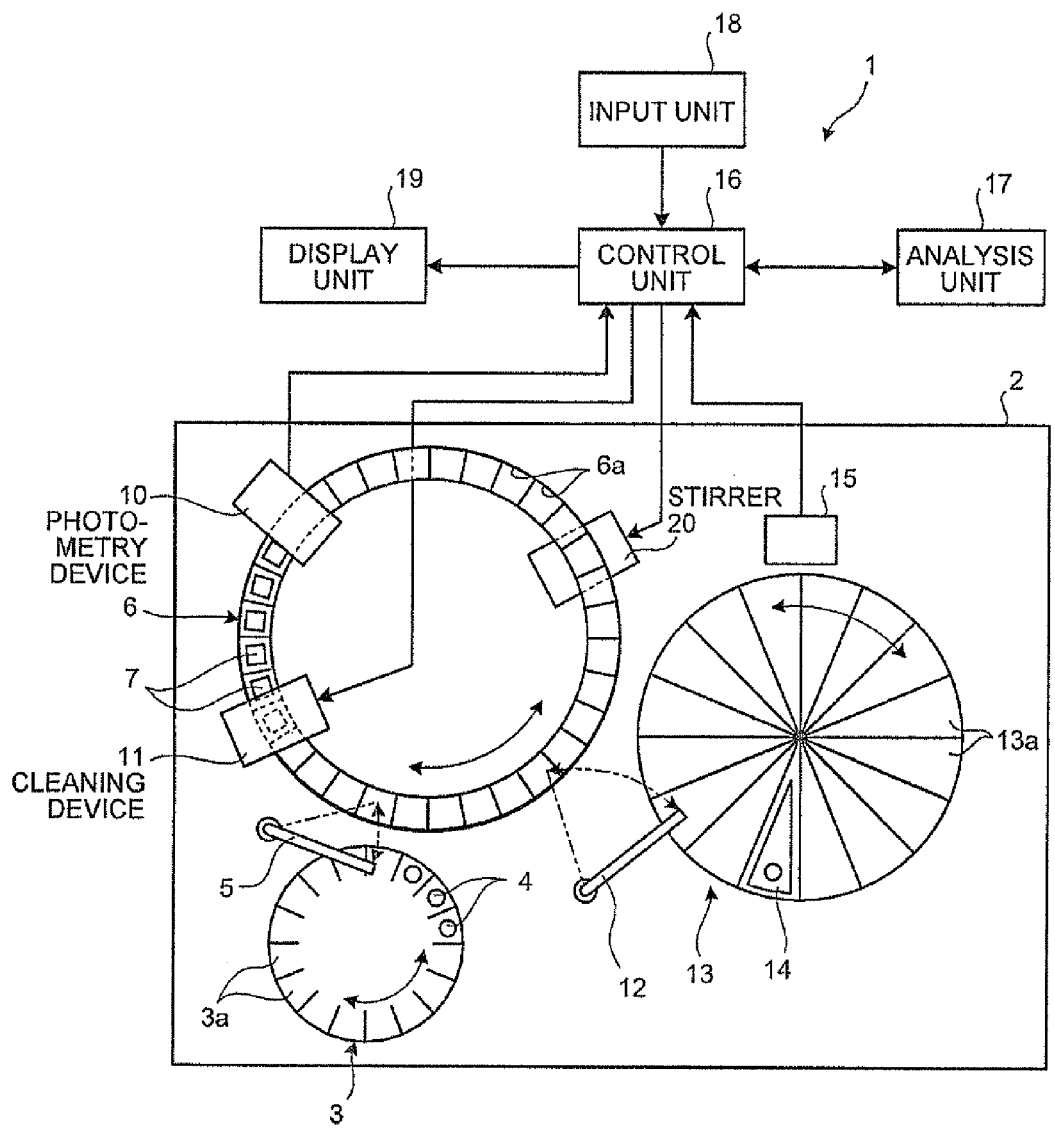
FIG. 1 is an outline configuration diagram showing an automatic analyzer in a first embodiment.
Figure 2:
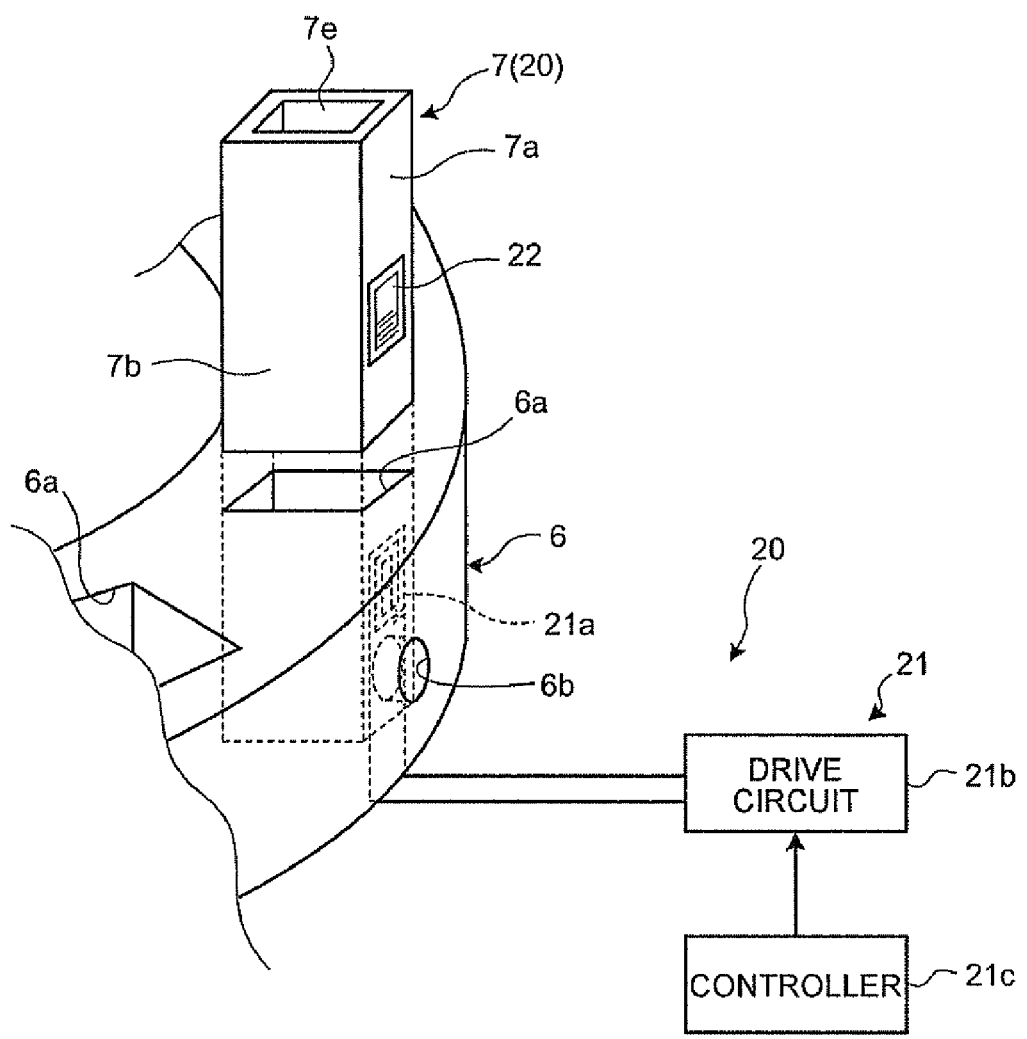
FIG. 2 is a perspective view showing a portion of a reaction vessel and a reaction wheel used in the automatic analyzer in the first embodiment together with an outline configuration diagram of a stirrer.
Figure 3:
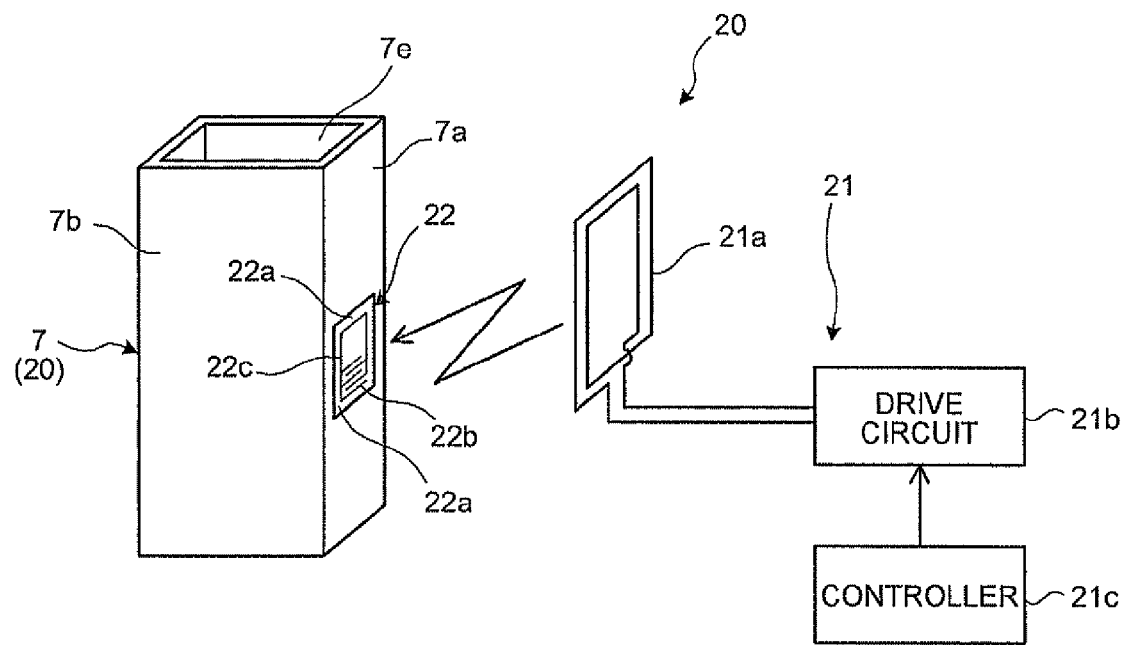
FIG. 3 is a block diagram showing the configuration of the stirrer in the first embodiment together with a perspective view of the reaction vessel.
Figure 4:
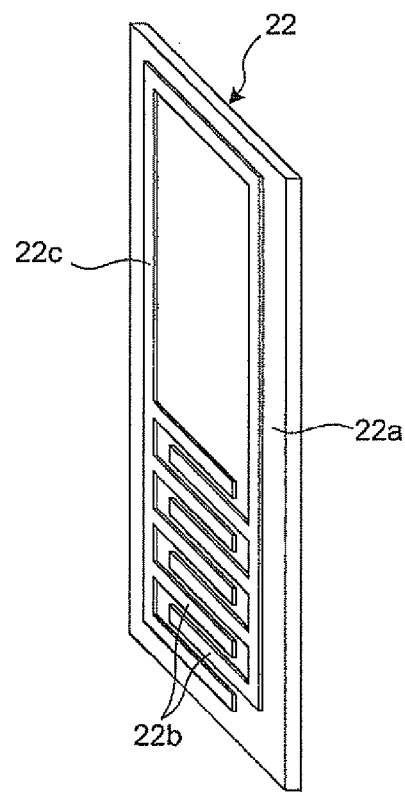
FIG. 4 is a perspective view of a surface acoustic wave device to be mounted on a sidewall of the reaction vessel in FIG. 3.

Embodiments of a stirrer and an analyzer of the present invention will be described in detail below with reference to drawings. FIG. 1 is an outline configuration diagram showing an automatic analyzer in a first embodiment. FIG. 2 is a perspective view showing a portion of a reaction vessel and a reaction wheel used in the automatic analyzer in the first embodiment together with an outline configuration diagram of a stirrer. FIG. 3 is a block diagram showing the configuration of the stirrer in the first embodiment together with a perspective view of the reaction vessel. FIG. 4 is a perspective view of a surface acoustic wave device to be mounted on a sidewall of the reaction vessel in FIG. 3.

An automatic analyzer 1 includes, on a work table 2 as shown in FIG. 1, a specimen table 3, a specimen dispensing mechanism 5, a reaction wheel 6, a photometry device 10, a cleaning device 11, a reagent dispensing mechanism 12, and a reagent table 13, and a stirrer 20 provided therein.

As shown in FIG. 1, the specimen table 3 is rotated by a drive means in directions indicated by arrows and a plurality of storage chambers 3a arranged on an outer circumference along a circumferential direction at equal intervals is provided. In each storage chamber 3a, a specimen vessel 4 housing a specimen is freely detachably stored.

The specimen dispensing mechanism 5 is a means for dispensing a specimen to a plurality of reaction vessels 7 held in the reaction wheel 6 and, as shown in FIG. 1, successively dispenses specimens from a plurality of the specimen vessels 4 on the specimen table 3 to a reaction vessel 7.

The reaction wheel 6 is rotated by a drive means that is different from that of the specimen table 3 in directions indicated by arrows and a plurality of recesses 6a is provided on the outer circumference along the circumferential direction at equal intervals. The reaction wheel 6 has openings 6b (See FIG. 2) through which a measuring beam passes formed on both sides in a radial direction of each of the recesses 6a. The reaction wheel 6 rotates clockwise by (one round–one reaction vessel)/4 in one cycle and rotates counterclockwise by one recess 6a in four cycles. The reaction wheel 6 has the photometry device 10 and the cleaning device 11 arranged on a rotation path and the stirrer 20 arranged below a position opposite to the cleaning device 11 in a diameter direction.

The reaction vessel 7 is a small vessel of several nL (nanoliters) to several tens of µL (microliters) in volume and uses a transparent material that allows to pass 80% or more of light contained in an analytical beam (340 to 800 nm) emitted from a light source of the photometry device 10, for example, glass including heat-resistant glass and synthetic resin such as cyclic olefine and polystyrene. As shown in FIG. 2 and FIG. 3, the reaction vessel 7 is a cuvette in a rectangular cylindrical shape forming a liquid holding unit 7d whose horizontal section is square to hold a liquid by sidewalls 7a and 7b and a bottom wall 7c (See FIG. 5) and having an opening 7e in an upper part of the liquid holding unit 7d. The reaction vessel 7 constitutes the stirrer 20 together with a surface acoustic wave device 22 mounted on the sidewall 7a and inner walls of the liquid holding unit 7d are treated to have an affinity for liquids of specimens or reagents. The reaction vessel 7 is arranged in the recess 6a with the sidewall 7a directed in the radial direction of the reaction wheel 6 and the sidewall 7b directed in the circumferential direction of the reaction wheel 6.

The photometry device 10 is arranged, as shown in FIG. 1, near the outer circumference of the reaction wheel 6 and has the light source emitting the analytical beam (340 to 800 nm) for analyzing a liquid held in the reaction vessel 7 and a photo detector for receiving the analytical beam after being passed through the liquid by dispersing the analytical beam. The photometry device 10 is arranged in such a way that the light source and the photo detector are positioned opposite to each other sandwiching the recess 6a of the reaction wheel 6.

The cleaning device 11 has a discharging means for discharging liquids and cleaning liquids from the reaction vessel 7 and a dispensing means for dispensing a cleaning liquid. After discharging a liquid after light measurement from the reaction vessel 7 after light measurement, the cleaning device 11 dispenses a cleaning liquid. By repeating an operation of dispensing and discharging of a cleaning liquid two or more times, the cleaning device 11 cleans an inner part of the reaction vessel 7. After being cleaned in this manner, the reaction vessel 7 is used again for analysis of a new specimen.

The reagent dispensing mechanism 12 is a means for dispensing a reagent to the plurality of reaction vessels 7 held by the reaction wheel 6 and, as shown in FIG. 1, successively dispenses a reagent from a predetermined reagent vessel 14 of a reagent table 13 to the reaction vessels 7.

The reagent table 13 is rotated by a drive means that is different from that of the specimen table 3 and the reaction wheel 6 in directions indicated by arrows and a plurality of storage chambers 13a formed in a fan shape is provided along the circumferential direction. The reagent vessel 14 is freely detachably stored in each of the storage chambers 13a. Each of a plurality of the reagent vessels 14 is filled with a predetermined reagent corresponding to each inspection item and an information recording medium (not shown) showing information about the housed reagent is attached to an outer surface thereof.

Here, as shown in FIG. 1, a reader 15 for reading information such as the type of reagent, lots, and term of validity recorded in the information recording medium attached to the reagent vessel 14 and outputting the information to a control unit 16 is set up on the outer circumference of the reagent table 13.

The control unit 16 is connected to the specimen table 3, the specimen dispensing mechanism 5, the reaction wheel 6, the photometry device 10, the cleaning device 11, the reagent dispensing mechanism 12, the reagent table 13, the reader 15, an analysis unit 17, an input unit 18, a display unit 19, and the stirrer 20 and, for example, a microcomputer equipped with a storage function to store analysis results is used as the control unit 16. The control unit 16 controls actuation of each unit of the automatic analyzer 1 and, if the lot or term of validity is outside the range of setup based on information read from records in the information recording medium, controls the automatic analyzer 1 to stop analysis work or issues an warning to the operator.

The analysis unit 17 is connected to the photometry device 10 via the control unit 16, analyzes constituent concentrations and the like in a specimen from the rate of absorption of a liquid inside the reaction vessel 7 based on the quantity of light received by the photo detector, and then outputs an analysis result to the control unit 16. The input unit 18 is a part where operations to input inspection items and the like into the control unit 16 are performed and, for example, a keyboard or a mouse is used as the input unit 18. The display unit 19 displays analysis content, warnings and the like and a display panel or the like is used as the display unit 19.

The stirrer 20 stirs a liquid held in the reaction vessel 7 by sound waves generated by driving the surface acoustic wave device 22 and, as shown in FIG. 2 and FIG. 3, in addition to the reaction vessel 7, has a power transmitter 21 for supplying power to the surface acoustic wave device 22 and the surface acoustic wave device 22.

The power transmitter 21 has an RF transmitting antenna 21a, a drive circuit 21b, and controller 21c. The power transmitter 21 sends power supplied from a high-frequency AC source of several MHz to several hundreds of MHz from the RF transmitting antenna 21a to the surface acoustic wave device 22 as a drive signal. The RF transmitting antenna 21a is mounted on the sidewall of the recess 6a of the reaction wheel 6.

The drive circuit 21b has an oscillating circuit capable of changing oscillating frequencies based on a control signal from the controller 21c and outputs a high-frequency oscillating signal of several tens to several hundreds of MHz to the RF transmitting antenna 21a. Here, the RF transmitting antenna 21a and the drive circuit 21b are connected via a contact electrode so that power can still be supplied even if the reaction wheel 6 rotates. Thus, in the power transmitter 21, the RE transmitting antenna 21a to which power is supplied via the contact electrode switches as the reaction wheel 6 rotates and the liquid held in the reaction vessel 7 of each of the recesses 6a is successively stirred. The controller 21c controls actuation of the drive circuit 21b and controls, for example, characteristics (characteristics of the frequency, intensity, phase, and waves), waveforms (such as sine waves, triangular waves, rectangular waves, and burst waves), and modulation (amplitude modulation and frequency modulation) of a sound wave emitted by the surface acoustic wave device 22. The controller 21c can also switch the frequency of oscillating signal emitted from the drive circuit 21b according to a built-in timer.

Figure 5:
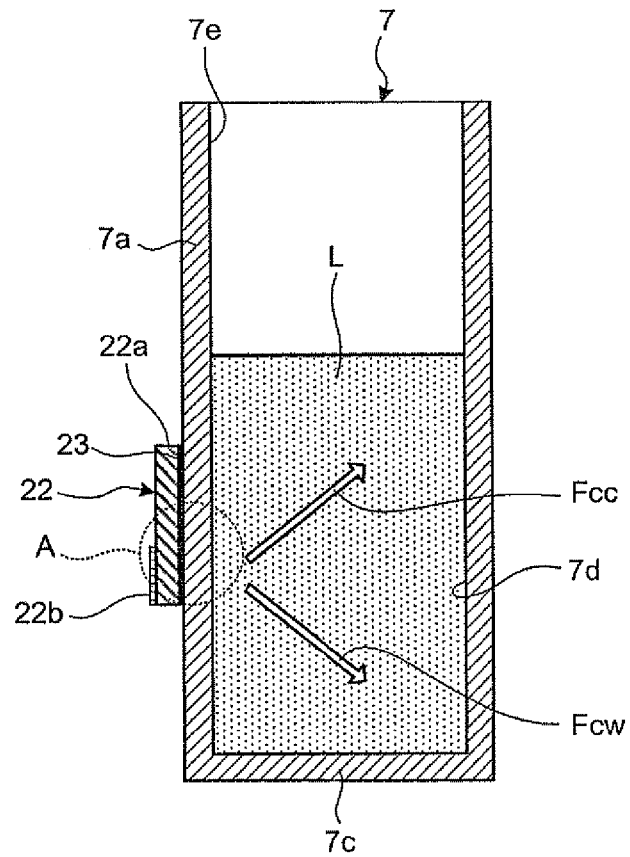
FIG. 5 is a sectional view of the reaction vessel shown in FIG. 3 showing a flow arising in a held liquid.
Figure 6:
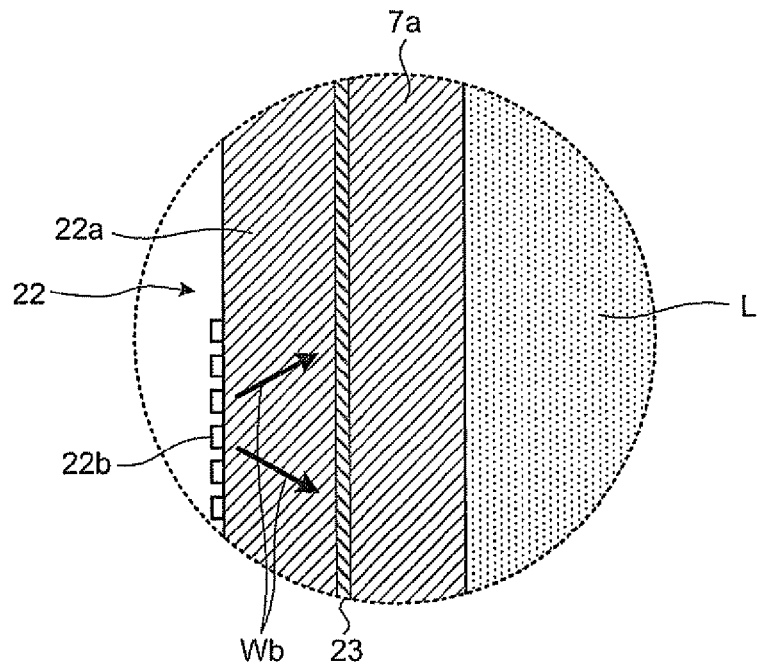
FIG. 6 is an enlarged cross-sectional view of an A portion of the reaction vessel shown in FIG. 5.

The surface acoustic wave device 22 is a sound wave generator for generating sound waves after receiving a drive signal (power) emitted from the RF transmitting antenna 21a. As shown in FIG. 3 and FIG. 4, the surface acoustic wave device 22 has a transducer 22b as being an interdigital transducer (IDT) and an antenna 22c formed on a piezoelectric substrate 22a made of, for example, lithium niobate (LiNbO$_3$). The transducer 22b is a sound generating element generating sound waves after a drive signal (power) emitted from the RF transmitting antenna 21a being received by the antenna 22c. The transducer 22b is arranged outside the reaction vessel 7 adjacent to a liquid held by the reaction vessel 7 via the reaction vessel 7 and the piezoelectric substrate 22a. That is, as shown in FIG. 5 and FIG. 6, the surface acoustic wave device 22 is mounted on the sidewall 7a of the reaction vessel 7 via an acoustic matching layer 23 such as epoxy resin and ultraviolet curing resin with the transducer 22b directed outward. The surface acoustic wave device 22 is schematically depicted ignoring an actual thickness including the thickness of the acoustic matching layer 23, in addition to that of the piezoelectric substrate 22a, the transducer 22b, and antenna 22c to clarify the configuration. This also applies to other embodiments.

Here, it is desirable that the reaction vessel 7 and the piezoelectric substrate 22a overlap with each other and the surface thereof is processed smooth so that the surface roughness of the surface through which sound waves pass becomes smaller than the wavelength of sound waves generated by the transducer 22b. If the surface roughness of the surface through which sound waves pass of the reaction vessel 7 and the piezoelectric substrate 22a is larger than the wavelength of sound waves generated by the transducer 22b, generated sound waves are scattered by the surface of the reaction vessel 7 and the piezoelectric substrate 22a and, as a result, sound waves will not be emitted in a fixed direction shown in FIG. 6, leading to lower stirring efficiency of a liquid held in the reaction vessel 7.

In the automatic analyzer 1 configured as described above, the reagent dispensing mechanism 12 successively dispenses reagents to the plurality of reaction vessels 7 being transported along the circumferential direction by the rotating reaction wheel 6 from the reagent vessel 14. The reaction vessel 7 to which a reagent has been dispensed is transported along the circumferential direction by the rotating reaction wheel 6 to successively dispense specimens by the specimen dispensing mechanism 5 from the plurality of specimen vessels 4 held on the specimen table 3. Then, the reaction vessel 7 to which a specimen has been dispensed is transported to the stirrer 20 by the reaction wheel 6 so that the dispensed reagent and specimen are successively stirred to cause a reaction. A reaction mixture after the specimen and reagent are caused to react in this manner passes through the photometry device 10 when the reaction wheel 6 rotates again and an analytical beam emitted from the light source is transmitted. At this point, the reaction mixture of the specimen and reagent inside the reaction vessel 7 is measured by a light receiving unit and constituent concentrations and the like are analyzed by the control unit 16. Then, after the analysis is completed, the reaction vessel 7 is cleaned by the cleaning device 11 before being reused for analysis of another specimen.

At this point, in the stirrer 20, based on a control signal input from the input unit 18 in advance via the control unit 16, the controller 21c inputs a drive signal into the drive circuit 21b while the reaction wheel 6 stops. The transducer 22b of the surface acoustic wave device 22 is thereby driven in accordance with the frequency of the input drive signal and, as shown in FIG. 6, a bulk wave $W_b$ is caused. The caused bulk wave $W_b$ is incident on the sidewall 7a of the reaction vessel 7 after propagating through the piezoelectric substrate 22a and the acoustic matching layer 23 and, after propagating through the sidewall 7a as shown by arrows, leaks out to a liquid L having a similar acoustic impedance.

As a result, as shown in FIG. 5, not only a flow Fcc obliquely upward from the transducer 22b, but also a flow Fcw obliquely downward from the transducer 22b is generated in the liquid L inside the reaction vessel 7 by the leaked-out bulk wave so that the liquid L containing the dispensed reagent and specimen is stirred.

At this point, the stirrer 20 has the surface acoustic wave device 22 mounted on the sidewall 7a across the acoustic matching layer 23 with the transducer 22b directed toward the sidewall 7a adjacent to the liquid L. Thus, the stirrer 20 and the automatic analyzer 1 can improve stirring efficiency of the liquid L by suppressing attenuation involved in propagation of sound waves because sound waves generated by the transducer 22b is incident on the adjacent liquid L through the sidewall 7a of the reaction vessel 7 and thus, the propagation path of sound waves is short. The surface acoustic wave device 22 has the transducer 22b arranged outside the piezoelectric substrate 22a and the transducer 22b is exposed to the air without being covered with a solid body and therefore, excitation of the transducer 22b is hard to control so that an energy loss during driving can be reduced to a low level.

Here, since shear elasticity is not generally present in gas flow and liquid flow, sound waves are longitudinal waves propagating as compressional waves. In contrast, in addition to longitudinal waves, transverse waves are also present in solids. If, on the other hand, sound waves are caused in the surface acoustic wave device 22 in which the transducer 22b is arranged outside the piezoelectric substrate 22a, sound waves to be generated must be bulk waves so that sound waves propagate from the transducer 22b into the piezoelectric substrate 22a to be incident on the sidewall 7a of the reaction vessel 7 via the acoustic matching layer 23. In such a case, a sound wave (a bulk wave) generated by the surface acoustic wave device 22 is emitted into the liquid L with a minimum propagation loss to stir the liquid L efficiently.

At this point, a sound wave generated by the transducer 22b propagates through a medium present on the propagation path with a small acoustic impedance difference. Thus, the stirrer 20 can provide efficient stirring by suitably selecting the medium present on the propagation path of the sound wave generated by the surface acoustic wave device 22 to make the acoustic impedance difference smaller and control propagation loss. In such a case, a first medium present on the propagation path of a sound wave generated by the transducer 22b has a plurality of sound wave modes and an acoustic impedance of each sound wave mode is substantially equal to at least one of acoustic impedances of a plurality of sound wave modes held by a second medium adjacent to the first medium.

In other words, in the stirrer 20, there are the piezoelectric substrate 22a as a first medium, the acoustic matching layer 23 as a second medium, the sidewall 7a of the reaction vessel 7 as a third medium, and the liquid L as a fourth medium on the propagation path of a sound wave generated by the transducer 22b of the surface acoustic wave device 22. At this point, as materials of these media, lithium niobate is assumed for the piezoelectric substrate 22a, ultraviolet curing resin for the acoustic matching layer 23, polystyrene resin for the reaction vessel 7, and water for the liquid L. Further, it is assumed that the density is ρ, the velocity of longitudinal waves is $V_L$, that of transverse waves is $V_S$, the impedance of longitudinal waves is $Z_L$ (=ρ·$V_L$), and that of transverse waves is ZS (=ρ·$V_S$).

Then, $ρ_B$=4.70 g/cm³, $V_{LB}$=4800 m/s, and $V_{SB}$=3500 m/s for the piezoelectric substrate 22a yield $Z_{LB}$=22.56 MRayl and $Z_{SB}$=16.45 MRayl. For the acoustic matching layer 23, $ρ_M$=1.15 g/cm³, $V_{LM}$=2600 m/s, and $V_{SM}$=1070 m/s yield $Z_{LM}$=2.99 MRayl and $Z_{SM}$=1.23 MRayl. For the reaction vessel 7, $ρ_C$=1.05 g/cm³, $V_{LC}$=2400 m/s, and $V_{SC}$=1070 m/s yield $Z_{LC}$=2.52 MRayl and $Z_{SC}$=1.12 MRayl. For the liquid L, $ρ_W$=1.00 g/cm³ and $V_{LW}$=1500 m/s yield $Z_{LW}$=1.5 MRayl.

Figure 7:
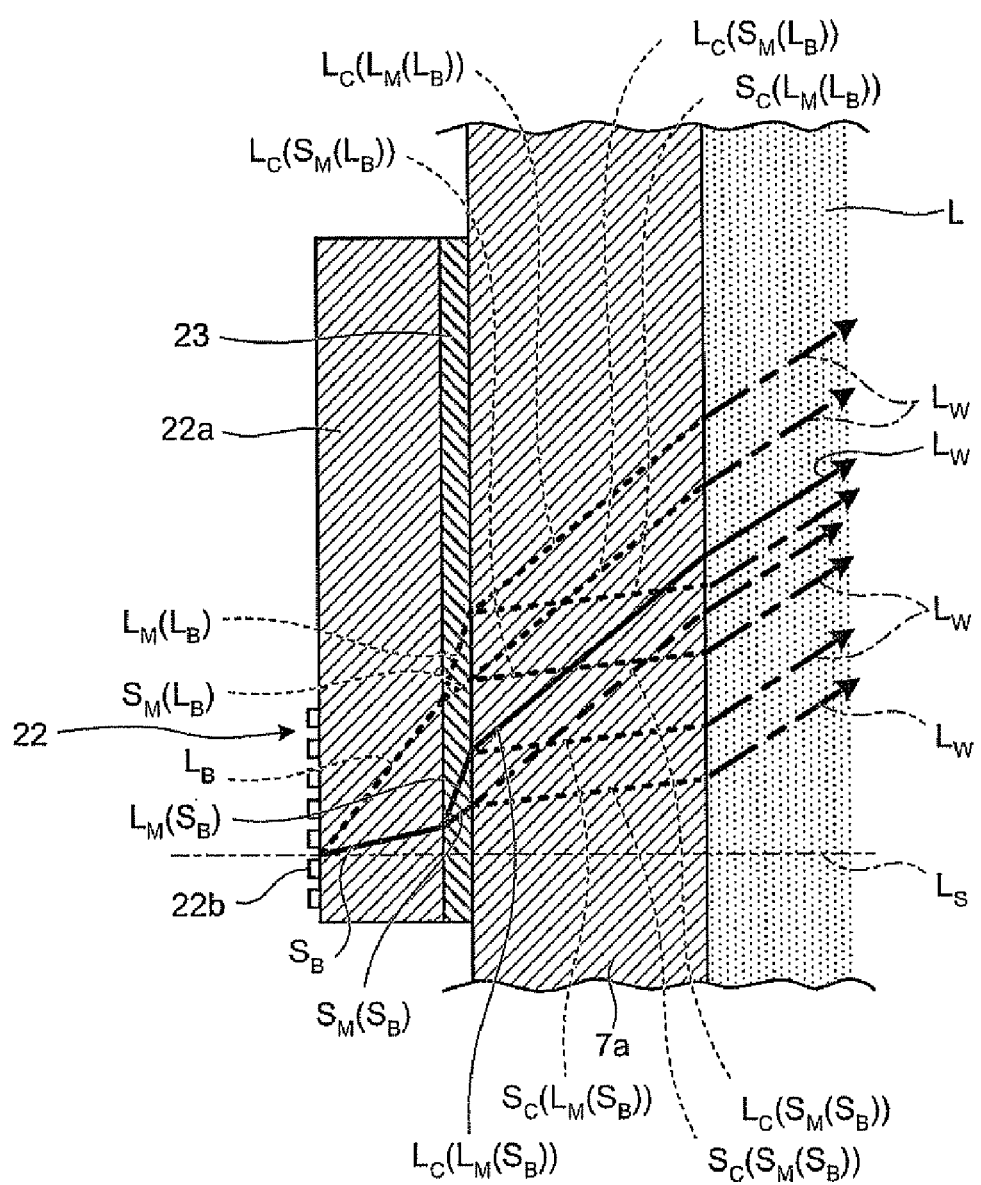
FIG. 7 is a diagram for illustrating acoustic impedance of media present on propagation paths of sound waves and propagation of longitudinal waves and transverse waves.

In this case, if the transducer 22b generates a sound wave, sound wave modes as shown in FIG. 7 are present in each medium. In the piezoelectric substrate 22a, two sound wave modes of longitudinal waves LB (ZLB=22.56 MRayl) and transverse waves SB (ZSB=16.45 MRayl) are present for sound waves. In the acoustic matching layer 23, two sound wave modes of longitudinal waves LM(LB), LM(SB) (ZLM=2.99 MRayl) and transverse waves SM(LB), SM(SB) (ZSM=1.23 MRayl) are present for sound waves. In the sidewall 7a of the reaction vessel 7, two sound wave modes of longitudinal waves LC(LM(LB)), LC(LM(SB)) (ZLC=2.52 MRayl) and transverse waves SC(LM(LB)), SC(LM(SB)) (ZSC=1.12 MRayl) originating from the longitudinal waves $L_M(L_B)$, $L_M(S_B)$ in the acoustic matching layer 23 and longitudinal waves $L_C(S_M(L_B))$, $L_C(S_M(S_B))$ ($Z_{LC}$=2.52 MRayl) and transverse waves $S_C(S_M(L_B))$, $S_C(S_M(S_B)$ ($Z_{SC}$=1.12 MRayl) originating from the transverse waves $S_M(L_B)$, $S_M(S_B)$ in the acoustic matching layer 23. Thus, an acoustic impedance of one sound wave mode held by the acoustic matching layer 23 becomes substantially equal to at least one of acoustic impedances of the plurality of sound wave modes held by the adjacent reaction vessels 7. Such longitudinal waves and transverse waves all become longitudinal waves $L_W$ after entering the liquid L. Here, if the transducer 22b is a bidirectional interdigital transducer, longitudinal waves and transverse waves in sound waves pass through the center of the transducer 22b to become symmetrical with respect to a line $L_s$ perpendicular to the plate surface of the piezoelectric substrate 22a in FIG. 7, but only longitudinal waves and transverse waves above the line Ls are shown to simplify the drawing.

Therefore, in the stirrer 20, if materials of the acoustic matching layer 23, the reaction vessel 7, and the liquid L are selected as described above, as shown in FIG. 7, mainly the transverse waves $S_B$ of sound waves generated by the transducer 22b are incident on the acoustic matching layer 23 from inside the piezoelectric substrate 22a due to a difference in acoustic impedance between adjacent media and propagates through the acoustic matching layer 23 mainly as the longitudinal waves $L_M(S_B)$ before being incident on the reaction vessel 7. Then, after propagating through the sidewall 7a of the reaction vessel 7, mainly as the longitudinal waves $L_C(L_M(S_B))$, the sound waves enters the liquid L in longitudinal waves $L_W$ mode. In this case, the longitudinal waves $L_B$ of sound waves generated by the transducer 22b also propagate through the piezoelectric substrate 22a, but it is difficult for the longitudinal waves LB to enter the acoustic matching layer 23 due to a large difference in acoustic impedance. Similarly, the transverse waves $S_M(S_B)$ propagating through the acoustic matching layer 23 enters the sidewall 7a also as the longitudinal waves $L_C(S_M(S_B))$, but it is difficult for the longitudinal waves $L_C(S_M(S_B))$ to enter sidewall 7a due to a large difference in acoustic impedance. Also similarly below, how easily longitudinal waves or transverse waves enter a medium can be determined based on the magnitude of a difference in acoustic impedance.

Here, the stirrer 20 in the present invention uses an interdigital transducer (IDT) as the transducer 22b of the surface acoustic wave device 22 and thus, the structure thereof is simple and particularly the portion of the transducer 22b can be made thin. The surface acoustic wave device 22 is also fixed to the reaction vessel 7 and thus, the stirrer 20 can easily handle the surface acoustic wave device 22 together with the reaction vessel 7.

Figure 8:
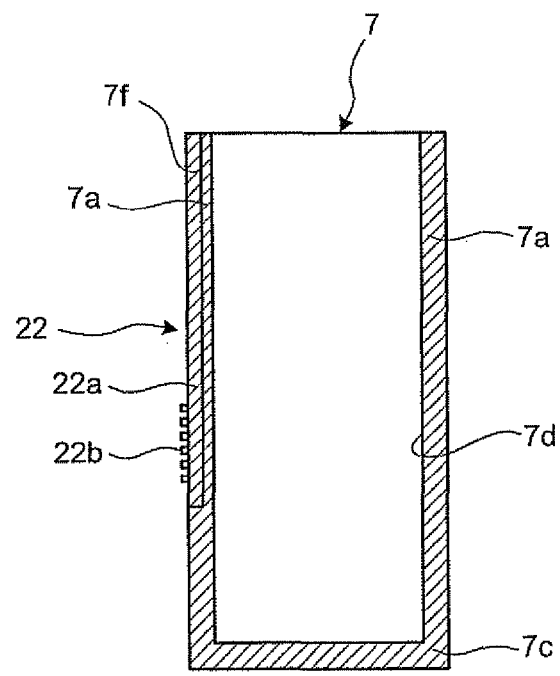
FIG. 8 is a sectional view showing a first modification of the reaction vessel used in the stirrer in the first embodiment.
Figure 9:
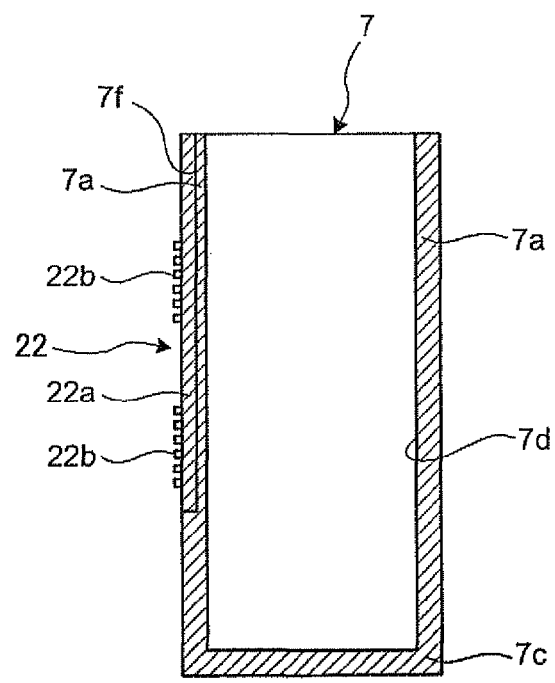
FIG. 9 is a sectional view showing a second modification of the reaction vessel used in the stirrer in the first embodiment.

Therefore, as shown in FIG. 8, the stirrer 20 may use the reaction vessel 7 obtained by embedding the surface acoustic wave device 22 in a recess 7f formed by making the sidewall 7a thinner across an acoustic matching layer with the transducer 22b being directed outward from the reaction vessel 7. In this case, as shown in FIG. 9, the stirrer 20 may have two units of the transducer 22b of the surface acoustic wave device 22 mounted on the reaction vessel 7. If there are two units, the stirrer 20 can improve stirring capabilities by using the two transducers 22b in various combinations such as driving the two transducers 22b in a time-division fashion and driving simultaneously the two transducers 22b with different center frequencies. Therefore, even if the number of liquids held is large, the liquids can be stirred in a short time.

Figure 10:
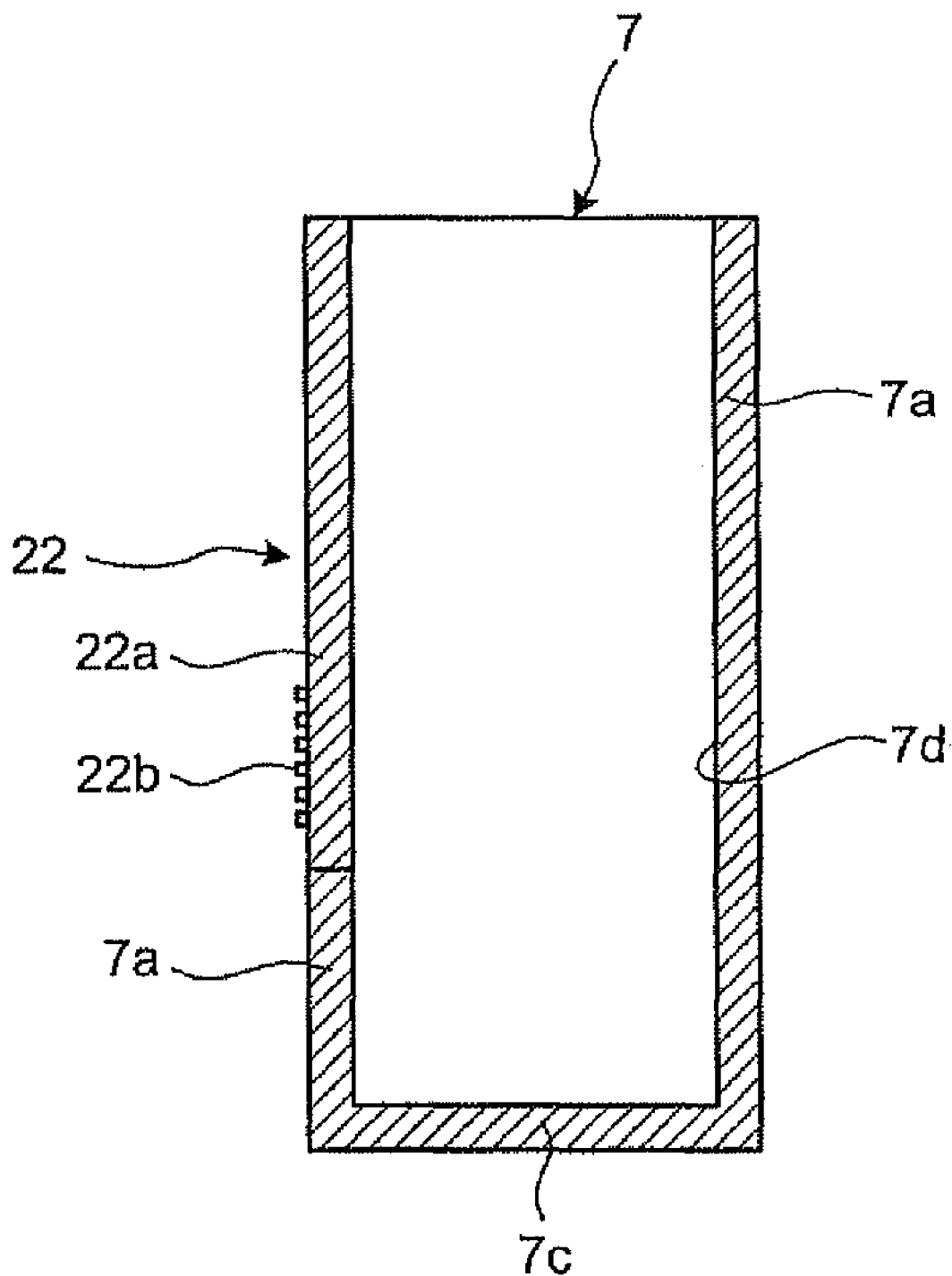
FIG. 10 is a sectional view showing a third modification of the reaction vessel used in the stirrer in the first embodiment.

The surface acoustic wave device 22 can be constructed to be smaller and therefore, the stirrer 20 may be constructed, like the reaction vessel 7 shown in FIG. 10, by using the surface acoustic wave device 22 as a portion of the sidewall 7a and embedding the surface acoustic wave device 22 in an upper part of the sidewall 7a with the transducer 22b being directed outward from the reaction vessel 7.

Figure 11:
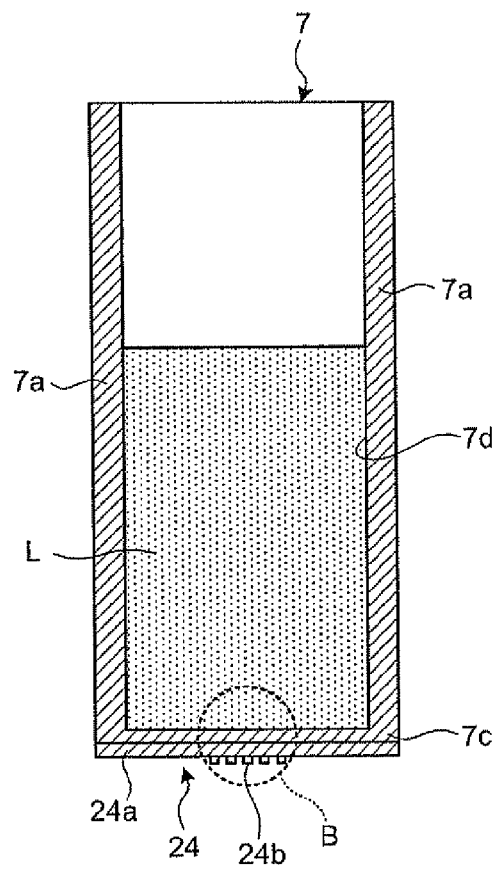
FIG. 11 is a sectional view showing a fourth modification of the reaction vessel used in the stirrer in the first embodiment.
Figure 12:
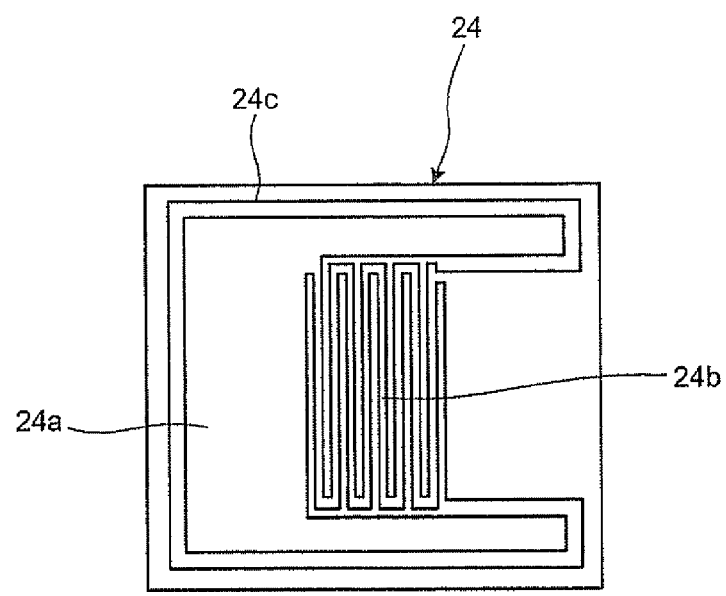
FIG. 12 is a front view of a surface acoustic wave device used in the reaction vessel shown in FIG. 11.
Figure 13:
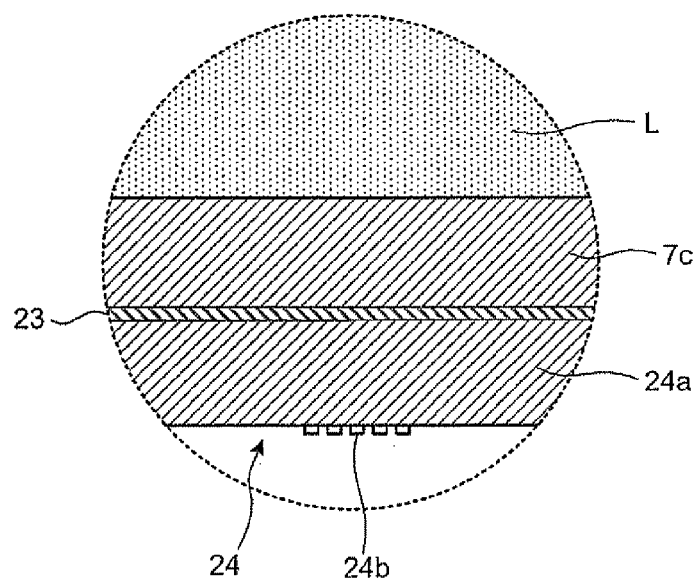
FIG. 13 is an enlarged view of a B portion of the reaction vessel shown in FIG. 11.

On the other hand, like the reaction vessel 7 shown in FIG. 11, the stirrer 20 may have a surface acoustic wave device 24 mounted on the undersurface of the bottom wall 7c. The surface acoustic wave device 24 has, as shown in FIG. 12, a transducer 24b as being an interdigital transducer (IDT) provided in the center of the surface of a substrate 24a and an antenna 24c to be a receiving means is integrally provided like enclosing the transducer 24b. In this case, as shown in FIG. 13, the surface acoustic wave device 24 is mounted on the bottom wall 7c across the acoustic matching layer 23 with the transducer 24b directed outward from the reaction vessel 7. The stirrer 20 has the RF transmitting antenna 21a of the power transmitter 21 provided on the bottom wall of the recess 6a of the reaction wheel 6.

Figure 14:
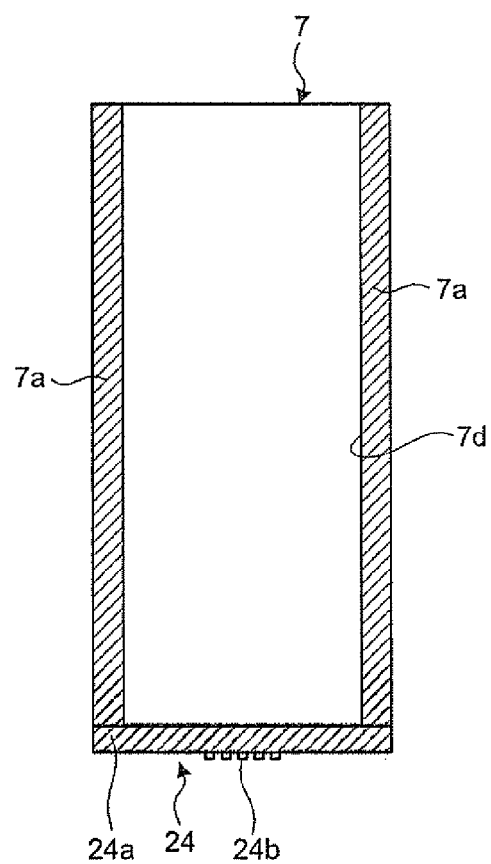
FIG. 14 is a sectional view showing a fifth modification of the reaction vessel used in the stirrer in the first embodiment.

Furthermore, like the reaction vessel 7 shown in FIG. 14, the stirrer 20 may use the piezoelectric substrate 24a of the surface acoustic wave device 24 as a bottom wall. In this case, the piezoelectric substrate 24a of the surface acoustic wave device 24 is mounted on a lower part of the sidewall 7a with the transducer 24b being directed outward from the reaction vessel 7.

Second Embodiment

Figure 15:
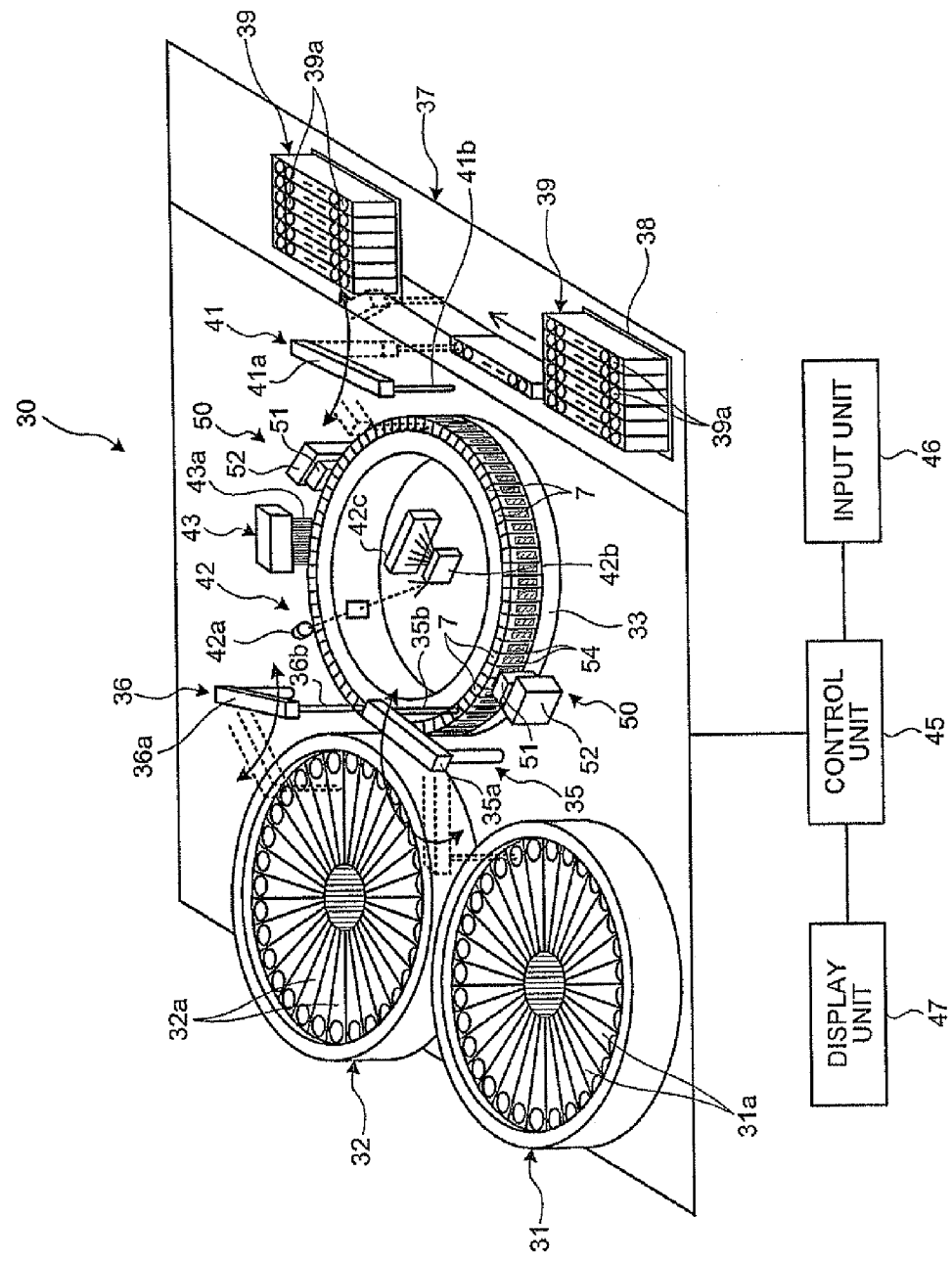
FIG. 15 is an outline configuration diagram of an automatic analyzer in a second embodiment equipped with a stirrer.
Figure 16:
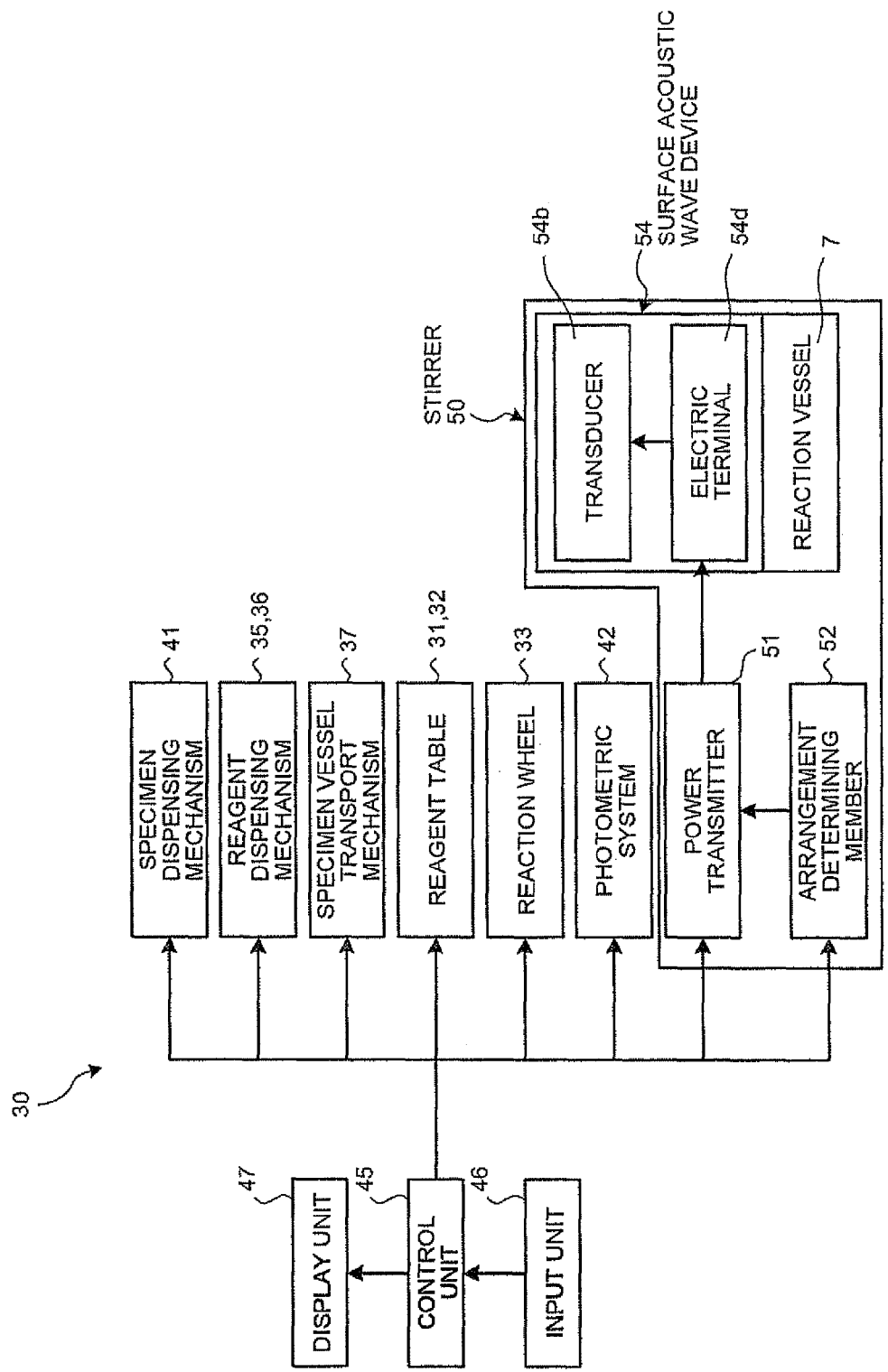
FIG. 16 is a block diagram showing the configuration of the automatic analyzer in FIG. 15.
Figure 17:
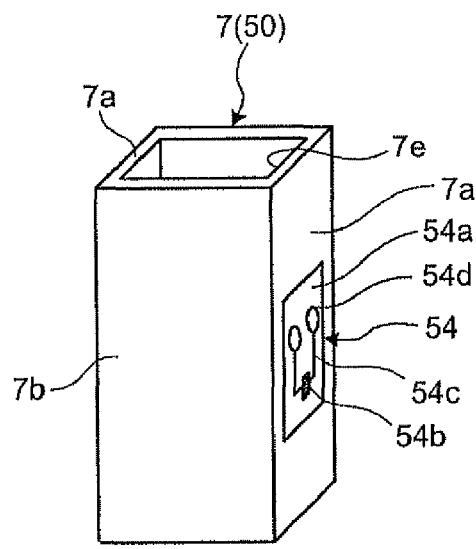
FIG. 17 is a perspective view showing a surface acoustic wave device of the stirrer used in the automatic analyzer in FIG. 15 and a reaction vessel on which the surface acoustic wave device is mounted.
Figure 18:
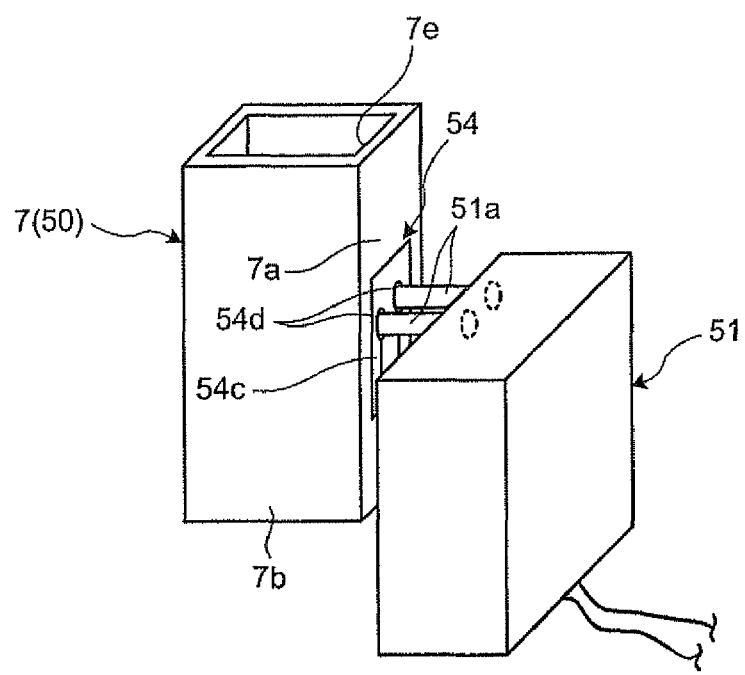
FIG. 18 is a perspective view showing the reaction vessel on which the surface acoustic wave device is mounted and used in the automatic analyzer in FIG. 15 together with a power transmitter.

Next, a second embodiment of a stirrer and an analyzer of the present invention will be described in detail with reference to drawings. While power is supplied to the surface acoustic wave device by radio in the first embodiment, power is supplied to the surface acoustic wave device through a wire in the second embodiment. FIG. 15 is an outline configuration diagram of an automatic analyzer in the second embodiment equipped with a stirrer. FIG. 16 is a block diagram showing the configuration of the automatic analyzer in FIG. 15. FIG. 17 is a perspective view showing a surface acoustic wave device of the stirrer used in the automatic analyzer in FIG. 15 and a reaction vessel on which the surface acoustic wave device is mounted. FIG. 18 is a perspective view showing the reaction vessel on which the surface acoustic wave device is mounted and used in the automatic analyzer in FIG. 15 together with a power transmitter. Here, in the automatic analyzer in the second embodiment, the stirrer uses the same reaction vessel as the stirrer 20 in the first embodiment and thus, the same numerals are used to describe the reaction vessel.

An automatic analyzer 30 has, as shown in FIG. 15 and FIG. 16, reagent tables 31, 32, a reaction wheel 33, a specimen vessel transport mechanism 37, a photometric system 42, a cleaning mechanism 43, a control unit 45, and a stirrer 50.

As shown in FIG. 15, each of the reagent tables 31, 32 holds a plurality of reagent vessels 31a, 32a arranged in the circumferential direction and transports the reagent vessels 31a, 32a in the circumferential direction by being rotated by a drive means (not shown) respectively.

As shown in FIG. 15, the reaction wheel 33 has the plurality of reaction vessels 7 arranged along the circumferential direction and transports the reaction vessels 7 by being rotated normally or reversely by a drive means (not shown). Reagents are dispensed to the reaction vessels 7 by reagent dispensing mechanism 35, 36 provided nearby from the reagent vessels 31a, 32a of the reagent tables 31, 32. Here, the reagent dispensing mechanisms 35, 36 have probes 35b, 36b provided for dispensing reagents to arms 35a, 36a rotating in arrow directions on a horizontal plane and have a cleaning means for cleaning the probes 35b, 36b with washing water respectively.

As shown in FIG. 16 and FIG. 17, the reaction vessel 7 constitutes the stirrer 50 together with a surface acoustic wave device 54 mounted on the sidewall 7a.

As shown in FIG. 15, the specimen vessel transport mechanism 37 is a transport means for transporting a plurality of racks 39 arranged in a feeder 38 along an arrow direction one by one and transports the rack 39 step by step. The rack 39 holds a plurality of specimen vessels 39a housing specimens. Here, each time the step of the rack 39 transported by the specimen vessel transport mechanism 37 stops, specimens in the specimen vessels 39a are dispensed to each of the reaction vessels 7 by a specimen dispensing mechanism 41 having a drive arm 41a rotating in a horizontal direction and a probe 41b. Thus, the specimen dispensing mechanism 41 has a cleaning means (not shown) for cleaning the probe 41b with washing water.

The photometric system 42 emits an analytical beam (340 to 800 nm) for analyzing a liquid in the reaction vessel 7 after a reagent and specimen have reacted and has, as shown in FIG. 15, a light emitting unit 42a, a dispersing unit 42b, and a light receiving unit 42c. An analytical beam emitted from the light emitting unit 42a passes through the liquid in the reaction vessel 7 before being received by the light receiving unit 42c provided at a position opposite to the dispersing unit 42b. The light receiving unit 42c is connected to the control unit 45.

After suctioning and discharging the liquid in the reaction vessel 7 with a nozzle, the cleaning mechanism 43 repeatedly injects and discharges a detergent and a cleaning liquid such as washing water through the nozzle 43a to clean the reaction vessel 7 after analysis by the photometric system 42 is completed.

The control unit 45 controls actuation of each unit of the automatic analyzer 30 and also analyzes constituent concentrations and the like in a specimen from the rate of absorption of the liquid inside the reaction vessel 7 based on the quantity of light emitted by the light emitting unit 42a and that received by the light receiving unit 42c and, for example, a microcomputer is used as control unit 45. As shown in FIG. 15 and FIG. 16, the control unit 45 is connected to an input unit 46 such as a keyboard and a display unit 47 such as a display panel.

The stirrer 50 stirs a liquid held in the reaction vessel 7 by a sound wave generated by driving the surface acoustic wave device 54 and has, in addition to the reaction vessel 7, as shown in FIG. 15 and FIG. 16, a power transmitter 51 and the surface acoustic wave device 54. The power transmitter 51 is arranged at a position on the outer circumference of the reaction wheel 33 opposite to the reaction vessel 7 in the horizontal direction and sends power supplied from a high-frequency AC source of several MHz to several hundreds of MHz to the surface acoustic wave device 54. The power transmitter 51 is equipped with a drive circuit and a controller and, as shown in FIG. 18, has a brush-like contact 51a in contact with an electric terminal 54d of the surface acoustic wave device 54. In this case, as shown in FIG. 15, the power transmitter 51 is supported by an arrangement determining member 52 and supplies power from the contact 51a to the electric terminal 54d when the rotation of the reaction wheel 33 stops.

The arrangement determining member 52, whose actuation is controlled by the control unit 45, moves the power transmitter 51 when power is sent from the power transmitter 51 to the electric terminal 54d to adjust the relative configuration of the reaction wheel 33 relative to the power transmitter 51 and the electric terminal 54d in the circumferential and radial directions and, for example, a biaxial stage is used as the arrangement determining member 52. More specifically, when the reaction wheel 33 rotates and no power is supplied from the power transmitter 51 to the electric terminal 54d, actuation of the arrangement determining member 52 is stopped and maintains the power transmitter 51 and the electric terminal 54d at a fixed distance. When the reaction wheel 33 stops and power is supplied from the power transmitter 51 to the electric terminal 54d, the arrangement determining member 52 operates under control of the control unit 45 to move the power transmitter 51 to adjust the position along the circumferential direction of the reaction wheel 33 so that the power transmitter 51 and the electric terminal 54d are positioned opposite to each other and also determines the relative configuration of the power transmitter 51 and the electric terminal 54d by bringing the power transmitter 51 and the electric terminal 54d closer to bring the contact 51a into contact with the electric terminal 54d.

Here, the stirrer 50 may use the control unit 45 of the automatic analyzer 30 as an arrangement determination means to adjust the relation configuration of the power transmitter 51 and the electric terminal 54d along the circumferential direction of the reaction wheel 33 by controlling a drive means such as a motor rotary driving the reaction wheel 33 by the control unit 45. As mentioned above, it is only necessary for the arrangement determining member 52 to be able to at least adjust the relative configuration of the power transmitter 51 and the electric terminal 54d along the circumferential direction of the reaction wheel 33 so that the power transmitter 51 and the electric terminal 54d are positioned opposite to each other. On the other hand, the relative configuration of the power transmitter 51 and the electric terminal 54d is detected, for example, by providing a reflection sensor on the power transmitter 51 side and using reflection from reflectors provided at specific positions of the reaction vessel 7 or the surface acoustic wave device 54. At this point, data of the detected relative configuration is entered in the control unit 45.

Figure 19:
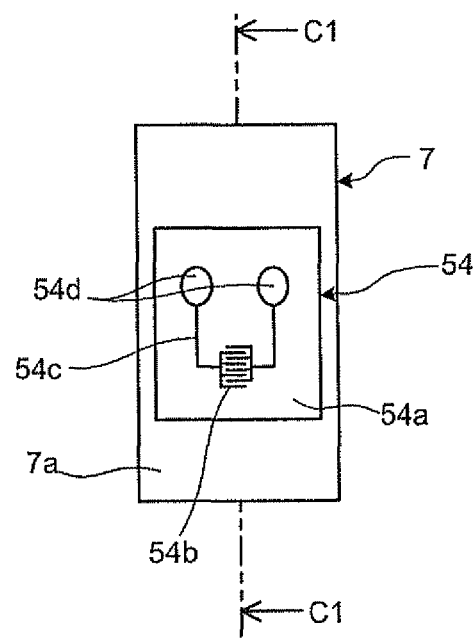
FIG. 19 is a front view of a reaction vessel on which a surface acoustic wave device is mounted.
Figure 20:
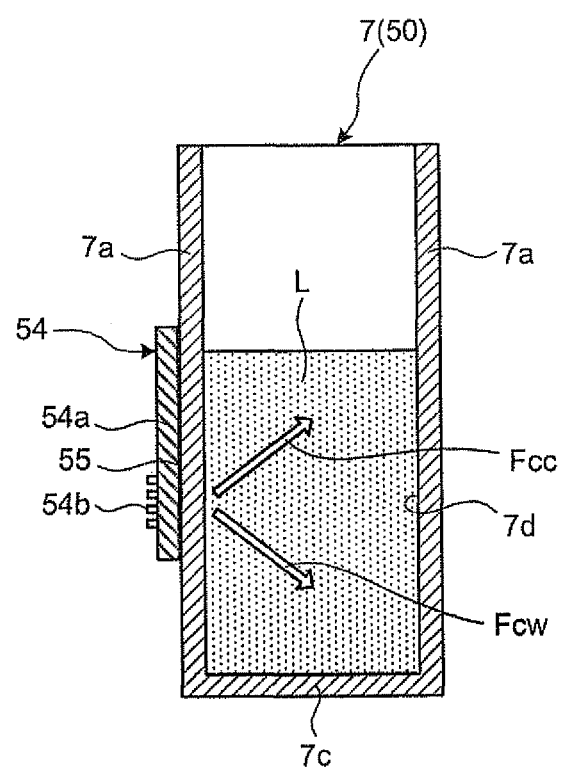
FIG. 20 is a sectional view along a C1-C1 line of the reaction vessel shown in FIG. 19.

As shown in FIG. 17 and FIG. 19, the surface acoustic wave device 54 is a sound wave generating means in which a transducer 54b as being an interdigital transducer (IDT) is provided on one surface of a piezoelectric substrate 54a and a bus bar 54c is extended to the surface on the other side with electric terminals 54d provided at ends of the bus bar 54c. The transducer 54b is a sound generating element generating sound waves by power supplied from the power transmitter 51. The surface acoustic wave device 54 is mounted on the sidewall 7a of the reaction vessel 7 so that when the reaction vessel 7 is set to the automatic analyzer 30, a plurality of comb-like electrodes constituting the transducer 54b is arranged in a vertical direction. The surface acoustic wave device 54 is mounted on the sidewall 7a of the reaction vessel 7 across an acoustic matching layer 55 (See FIG. 20) such as epoxy resin and ultraviolet curing resin with the transducer 54b directed outward from the reaction vessel 7.

At this point, as shown in FIG. 17, the surface acoustic wave device 54 including the electric terminals 54d to be a receiving means is arranged at an intermediate position in the vertical direction by avoiding a lower part of the sidewall 7a to be a window for light measurement so that light measurement by the photometric system 42 is not prevented. The surface acoustic wave device 54 uses an interdigital transducer (IDT) as the transducer 54b and thus, the structure thereof can be made simple with reduced size. Here, instead of lead zirconate titanate (PZT) attached with an interdigital transducer (IDT), PZT with electrodes on both sides may also be used for the transducer 54b.

In the automatic analyzer 30 configured as described above, the reagent dispensing mechanisms 35, 36 successively dispense reagents to the plurality of reaction vessels 7 operating under control of the control unit 45 and being transported along the circumferential direction by the rotating reaction wheel 33 from the reagent vessels 31a, 32a. Specimens are successively dispensed to the reaction vessels 7 to which reagents have been dispensed by the specimen dispensing mechanism 41 from the plurality of specimen vessels 39a held in the rack 39. Then, each time the reaction wheel 33 stops, the reaction vessels 7 to which reagents and specimens have been dispensed are successively stirred by the stirrer 50 to cause a reaction between reagents and specimens. When the reaction wheel 33 rotates again, the reaction vessels 7 pass through the photometric system 42. At this point, the liquid inside the reaction vessels 7 is measured photometrically by the light receiving unit 42c and constituent concentrations and the like are analyzed by the control unit 45. Then, after the analysis is completed, the reaction vessel 7 is cleaned by the cleaning mechanism 43 before being reused for analysis of another specimen.

At this point, in the stirrer, when the reaction wheel 33 stops, the power transmitter 51 supplies power from the contact 51a to the electric terminal 54d. The transducer 54b of the surface acoustic wave device 54 is thereby driven to cause sound waves. The caused sound waves propagate from the acoustic matching layer 55 into the sidewall 7a of the reaction vessel 7 before being leaked to a liquid having a similar acoustic impedance. As a result, as shown by arrows in FIG. 20, a flow $F_{cc}$ obliquely upward and a flow $F_{cw}$ obliquely downward arise from a position corresponding to the transducer 54b in the liquid L as a starting point inside the reaction vessel 7. The liquid L held inside the reaction vessel 7 is stirred by these two flows. At this point, the stirrer 50 brings the power transmission body 51 closer to the electric terminal 54d through the arrangement determining member 52 and also adjusts the positions so that the power transmitter 51 and the electric terminal 54d are opposite to each other and therefore, power transmission from the power transmitter 51 to the electric terminal 54d proceeds smoothly.

The reaction vessel 7 has the surface acoustic wave device 54 mounted on the sidewall 7a across the acoustic matching layer 55 (See FIG. 20) with the transducer 54b directed toward the sidewall 7a adjacent to the liquid L. Thus, in the stirrer 50 and the automatic analyzer 30, a sound wave generated by the transducer 54b enters the adjacent liquid L after passing through the sidewall 7a from the acoustic matching layer 55. Therefore, the stirrer 50 and the automatic analyzer 30 can improve stirring efficiency of the liquid L because the propagation path of sound waves is short and attenuation of sound waves involved in propagation can be suppressed.

Thus, the stirrer 50 is superior in propagation efficiency of sound waves generated by the surface acoustic wave device 54 and has a simple structure. As a result, the automatic analyzer 30 has an advantage that the automatic analyzer 30 can be reduced in size compared with conventional analyzers and maintenance thereof is made easier. The surface acoustic wave device 54 has the transducer 54b arranged outside the piezoelectric substrate 54a and the transducer 54b is exposed to the air without being covered with a solid body and therefore, excitation of the transducer 54b is hard to control so that an energy loss during driving can be reduced to a low level.

Figure 21:
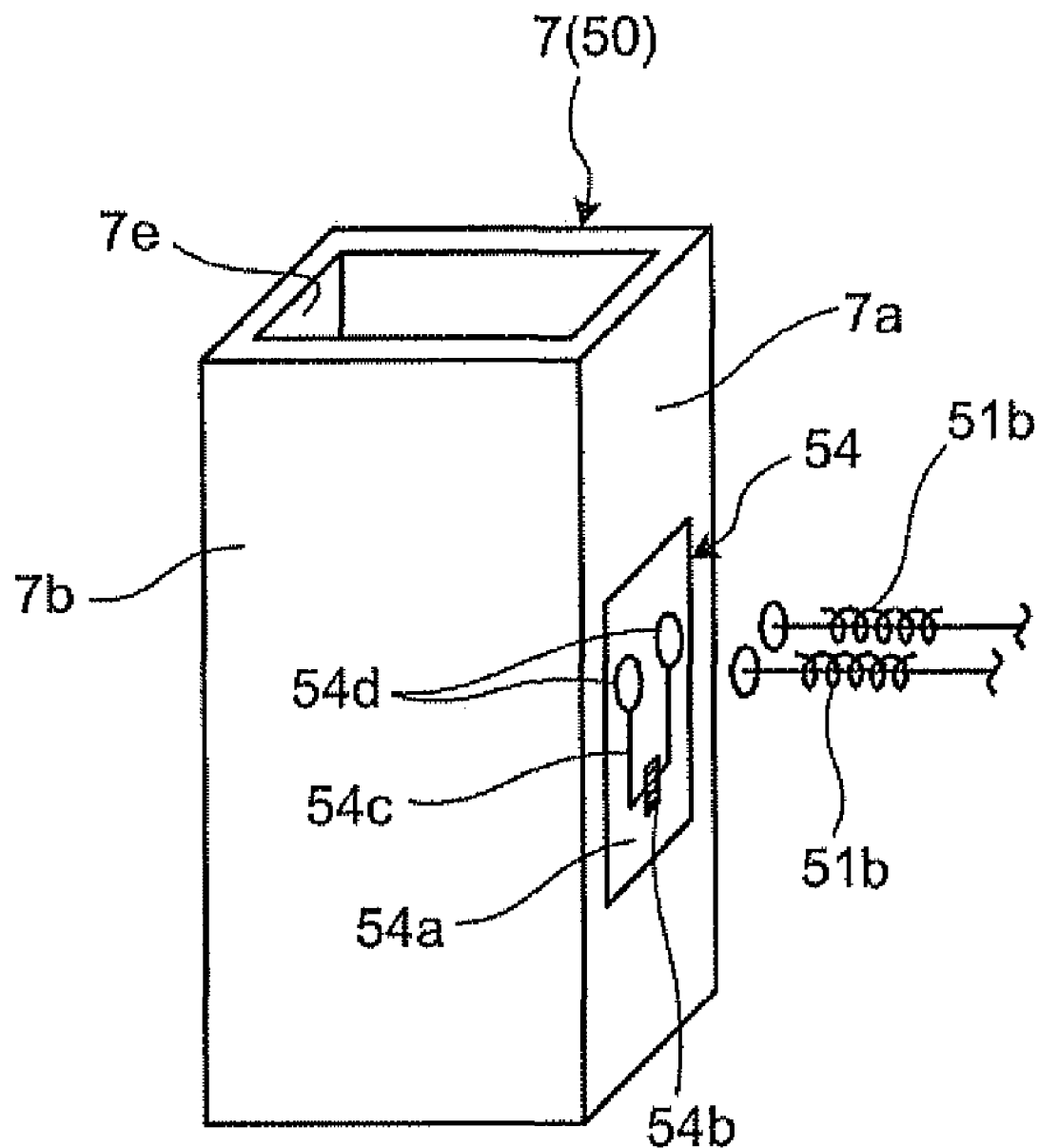
FIG. 21 is a perspective view of a modification of the power transmitter obtained by replacing contacts with spring terminals together with a reaction vessel.

The stirrer 50 in the second embodiment is constructed so that power is sent to the surface acoustic wave device 54 by the brush-like contact 51a being abutted the electric terminal 54d by the power transmitter 51. However, with respect to the stirrer 50, it may also be constructed that when power is sent to the surface acoustic wave device 54, the power transmitter 51 abuts the reaction vessel 7 with the arrangement determining member 52 having racks and pinions after the reaction wheel 33 stops and, as shown in FIG. 21, such as a spring terminal 51b provided in the power transmitter 51 abuts the electric terminal 54d. If this configuration is adopted, when the reaction vessels 7 are transported by rotating the reaction wheel 33, with the respect to the automatic analyzer 30, the power transmitter 51 is moved away from the reaction vessels 7 through the arrangement determining member 52 so that the spring terminal 51b should not interfere with the surface acoustic wave device 54.

Figure 22:
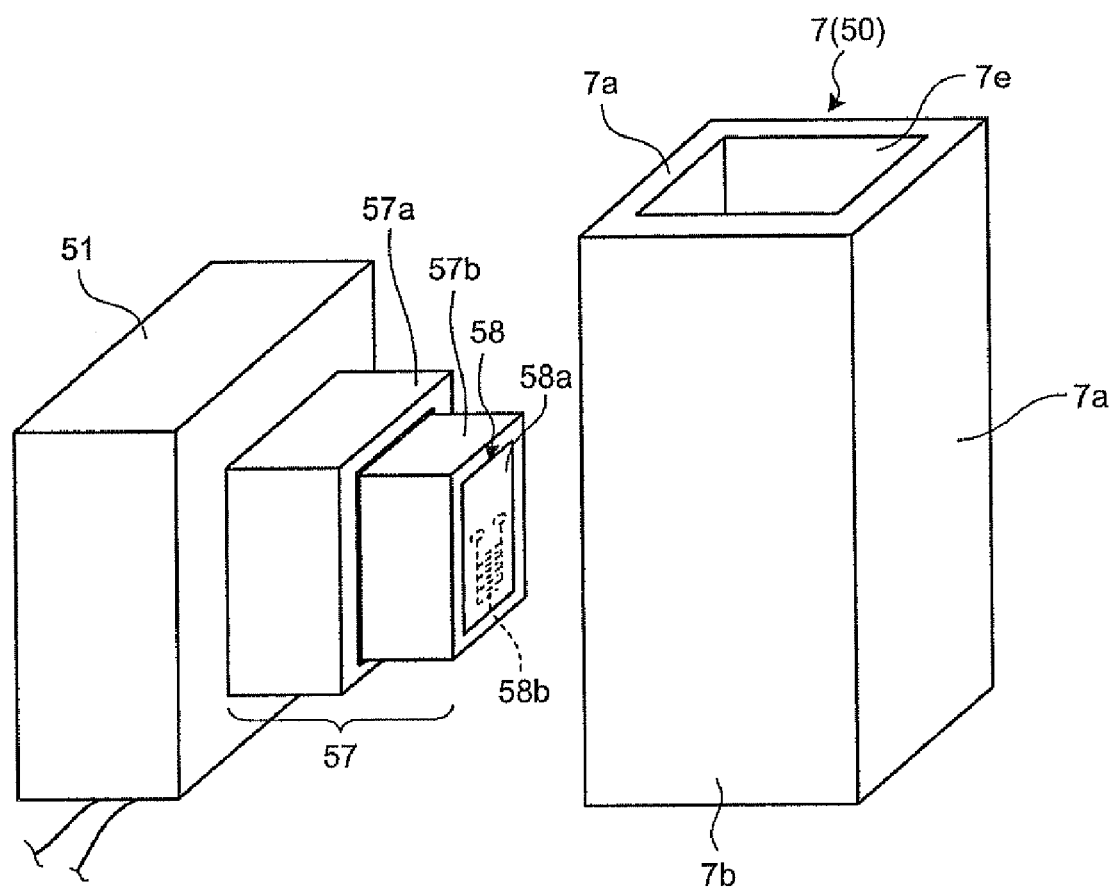
FIG. 22 is a perspective view showing a modification of the stirrer in the second embodiment.

The configuration of the stirrer 50 in which power is sent to the surface acoustic wave device 54 by the contact 51a abutting the electric terminal 54d by the power transmitter 51 may be changed and, for example, as shown in FIG. 22, an arm member 57 may be provided in the power transmitter 51 with a surface acoustic wave device 58 provided at a tip of the arm member 57 so that the surface acoustic wave device 58 comes into contact with the sidewall 7a of the reaction vessel 7 by the arm member 57 protruding when the liquid should be stirred.

With this configuration, the stirrer allows to suitably change the target on which a surface acoustic wave device should be mounted to the arm member 57 or the reaction vessel 7 in accordance with design, increasing design flexibility.

In this case, a drive arm 57b of the arm member 57 is freely appearingly/disappearingly supported by a support cylinder 57a. The surface acoustic wave device 58 has a transducer 58b formed on one surface of a piezoelectric substrate 58a, is glued to an end face of the drive arm 57b by an adhesive $A_d$ with the transducer 58b directly inward, and is driven by power supplied by a power line wired inside the support cylinder 57a and the drive arm 57b.

Figure 23:
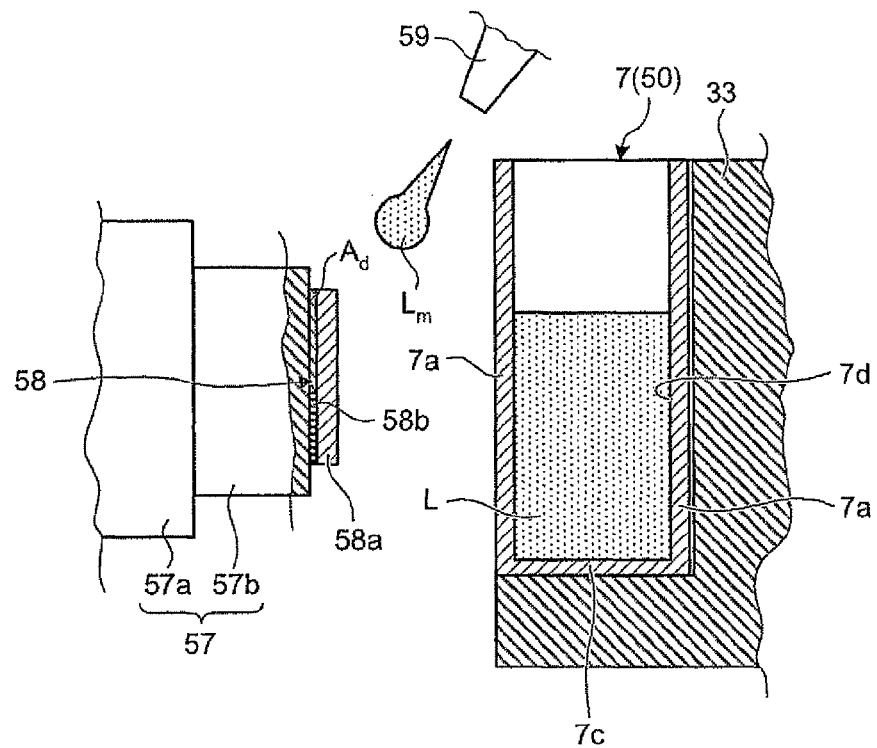
FIG. 23 is a diagram showing how an acoustic matching liquid is discharged to the surface acoustic wave device in the modification of the stirrer shown in FIG. 22 with portions of an arm member and a reaction wheel and a sectional view of the reaction vessel.
Figure 24:
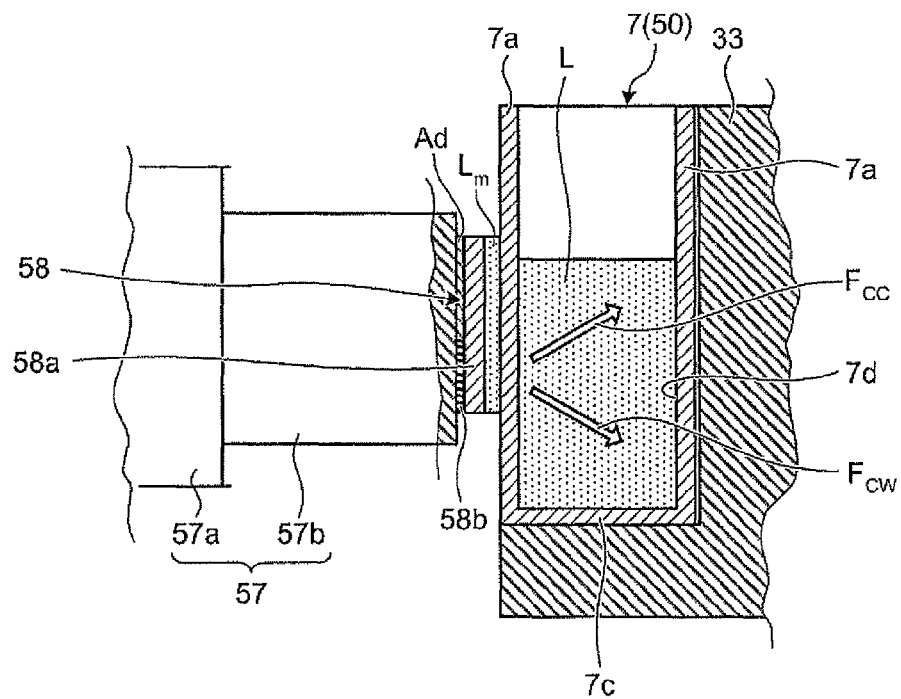
FIG. 24 is a diagram showing a state in which the surface acoustic wave device on an end face is brought into contact with a sidewall of the reaction vessel by a drive arm protruding in FIG. 23.

With the configuration as described above, for stirring by the surface acoustic wave device 58, as shown in FIG. 23, the stirrer 50 under control of the control unit 45 discharges an acoustic matching liquid $L_m$ to the surface acoustic wave device 58 from a nozzle 59 held by an acoustic matching liquid dispensing mechanism. Next, as shown in FIG. 24, the stirrer 50 under control of the control unit 45 protrudes the drive arm 57b to bring the surface acoustic wave device 58 on the end face of the drive arm 57b into contact with the sidewall 7a of the reaction vessel 7.

Accordingly, a sound wave (bulk wave) generated by the transducer 58b of the surface acoustic wave device 58 leaks out from the sidewall 7a of the reaction vessel 7 into the liquid L via a thin film of the acoustic matching liquid Lm arranged between the surface acoustic wave device 58 and the sidewall 7a. As a result, not only a flow Fcc obliquely upward from the transducer 58b, but also a flow Fcw obliquely downward from the transducer 58b arises in the liquid L by the leaked-out sound wave (bulk wave) so that the liquid L is stirred.

At this point, the stirrer 50 can improve stirring efficiency by suppressing attenuation of sound waves because the propagation path between where the surface acoustic wave device 58 comes into contact with the sidewall 7a via the acoustic matching liquid Lm and where the liquid L is irradiated with a sound wave (bulk wave) is short. Then, when stirring of the liquid L is completed, the stirrer 50 under control of the control unit 45 pulls back the drive arm 57b to end contact between the surface acoustic wave device 58 and the sidewall 7a of the reaction vessel 7.

The configuration of the stirrer 50 in which a surface acoustic wave device is abutted the sidewall 7a of the reaction vessel 7 to stir a liquid by the surface acoustic wave device is also applicable to the stirrer 20 in the first embodiment. In case of adopting such a configuration, it is necessary for the stirrer 20 to arrange the arm member 57 mounted the surface acoustic wave device 22 near the outer circumference of the reaction wheel 6, and also to form a contact opening above the opening 6b through which the drive arm 57b is inserted to make the surface acoustic wave device 22 abut the sidewall 7a of the reaction vessel 7.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stirrer, comprising:
   a vessel for holding a liquid to be stirred;
   a power transmitter, the power transmitter separated from the vessel; and
   a sound wave generator that utilizes received power from the power transmitter for irradiating the liquid with a sound wave to stir the liquid by the sound wave, wherein the sound wave generator is fixed to the vessel and includes
      an antenna configured to receive power from the power transmitter;
      a piezoelectric substrate, and
      a sound generating element provided on the piezoelectric substrate and arranged outside the vessel so as to be adjacent to the liquid across the vessel and the piezoelectric substrate to generate a sound wave for stirring the liquid.

2. The stirrer according to claim 1, wherein each of the vessel and the piezoelectric substrate have an overlapping surface through which the sound wave passes, the surface having a surface roughness smaller than a wavelength of the sound wave generated by the sound generating element.

3. The stirrer according to claim 1, wherein the sound generating element is an interdigital transducer.

4. The stirrer according to claim 1, wherein the sound wave is a bulk wave.

5. The stirrer according to claim 4, wherein
   a first medium present on a propagation path of the bulk wave generated by the sound generating element has a plurality of sound wave modes each having an acoustic impedance,
   a second medium adjacent to the first medium has a plurality of sound wave modes each having an acoustic impedance, and
   each acoustic impedance of the first medium is substantially equal to at least one of the acoustic impedances of the second medium.

6. The stirrer according to claim 1, wherein the power transmitter is configured to wirelessly transmit a signal.

7. The stirrer according to claim 6, wherein the power transmitter transmits a radio frequency.

8. The stirrer according to claim 1, further comprising two or more vessels.

9. The stirrer according to claim 8, wherein the power transmitter is configured to transmit power to a sound wave generator of a first vessel followed by transmitting power to a sound wave generator of a second vessel.

10. An analyzer for stirring and reacting different liquids to measure an optical property of a reaction liquid, and thus to analyze the reaction liquid, wherein the analyzer comprises a stirrer, the stirrer including;
    a vessel for holding a specimen and a reagent to be stirred;
    a power transmitter, the power transmitter separated from the vessel; and
    a sound wave generator that utilizes received power from the power transmitter for irradiating the liquid with a sound wave to stir the liquid by the sound wave, wherein the sound wave generator is fixed to the vessel and includes,
       an antenna configured to receive power from the power transmitter;
       a piezoelectric substrate, and
       a sound generating element provided on the piezoelectric substrate and arranged outside the vessel so as to be adjacent to the specimen and the reagent across the vessel and the piezoelectric substrate to generate a sound wave for stirring the specimen and the reagent.

11. The analyzer according to claim 10, wherein the power transmitter is configured to wirelessly transmit a signal.

12. The analyzer according to claim 11, wherein the power transmitter transmits a radio frequency.

13. The analyzer according to claim 10, further comprising two or more vessels.

14. The analyzer according to claim 13, wherein the power transmitter is configured to transmit power to a sound wave generator of a first vessel followed by transmitting power to a sound wave generator of a second vessel.

15. A stirrer, comprising:
a vessel for holding a liquid to be stirred;
one or more contact portions on a surface of the vessel;
one or more connections separable from the one or more contact portions for providing power from a power supply when the one or more connections are moved to contact the one or more contact portions; and
a sound wave generator that utilizes the provided power for irradiating the liquid with a sound wave to stir the liquid by the sound wave, wherein
the sound wave generator is fixed to the vessel and includes a piezoelectric substrate, and
a sound generating element provided on the piezoelectric substrate and arranged outside the vessel so as to be adjacent to the liquid across the vessel and the piezoelectric substrate to generate a sound wave for stirring the liquid.

16. The stirrer according to claim 15, wherein the one or more connections include a brush to contact the one or more contact portions.

17. The stirrer according to claim 15, wherein the one or more connections further comprises a biasing member for biasing the one or more contact portions when the one or more connections are moved to contact the one or more contact portions.

18. The stirrer according to claim 17, wherein the biasing member is a helical spring.

* * * * *